(12) United States Patent
Bogdan et al.

(10) Patent No.: US 6,177,601 B1
(45) Date of Patent: Jan. 23, 2001

(54) ISOMER-SELECTIVE AROMATIZATION PROCESS AND CATALYST

(75) Inventors: Paula L. Bogdan, Mount Prospect; Qianjun Chen, Des Plaines; Jaime G. Moscoso, Mount Prospect; Jeffery C. Bricker, Buffalo Grove, all of IL (US)

(73) Assignee: UOP LLC, Des Plaines, IL (US)

( * ) Notice: Under 35 U.S.C. 154(b), the term of this patent shall be extended for 0 days.

(21) Appl. No.: 09/318,583

(22) Filed: May 25, 1999

(51) Int. Cl.[7] ................ C07C 2/52; C07C 6/00; C10G 35/06
(52) U.S. Cl. ............ 585/419; 585/418; 208/138
(58) Field of Search .................. 585/414, 418; 208/138

(56) References Cited

U.S. PATENT DOCUMENTS

| | | | |
|---|---|---|---|
| 4,104,320 | 8/1978 | Bernard et al. | 260/673.5 |
| 4,634,518 * | 1/1987 | Buss et al. | 208/138 |
| 4,990,710 | 2/1991 | Dessau et al. | 585/277 |
| 5,124,497 * | 6/1992 | Dessau et al. | 585/419 |
| 5,518,708 | 5/1996 | Skeels et al. | 423/713 |

* cited by examiner

Primary Examiner—Marian C. Knode
Assistant Examiner—Thuan D. Dang
(74) Attorney, Agent, or Firm—John G. Tolomei; John F. Spears, Jr.

(57) ABSTRACT

An aromatization process, selective for the dehydrocyclization of paraffins to aromatics, is effected using a large-pore molecular-sieve catalyst containing a uniformly distributed platinum-group metal component, and a tin component incorporated into the large-pore molecular sieve by secondary synthesis. The use of this catalyst results in greater selectivity of conversion of paraffins to aromatics and in improved catalyst stability.

18 Claims, 7 Drawing Sheets

ISOMER-SELECTIVE AROMATIZATION PROCESS AND CATALYST

BACKGROUND OF THE INVENTION

1. Field of the Invention

This invention relates to a process and catalyst for the conversion of hydrocarbons, and more specifically for the aromatization of gasoline-range hydrocarbons.

2. General Background

The catalytic reforming of hydrocarbon feedstocks in the gasoline range is an important commercial process, practiced in nearly every significant petroleum refinery in the world to produce aromatic intermediates for the petrochemical industry or gasoline components with high resistance to engine knock. Demand for aromatics is growing more rapidly than the supply of feedstocks for aromatics production. Many large aromatics complexes have been completed recently or are under construction or planned which emphasize high yields of paraxylene as feedstock for polyester production to serve this burgeoning market. The catalytic reforming unit therefore must operate more efficiently at higher severity in order to meet these increasing needs for chemical aromatics while conserving feedstocks. This trend creates a need for more effective aromatization processes and catalysts.

Catalytic reforming generally is applied to a feedstock rich in paraffins and naphthenic hydrocarbons and is effected through diverse reactions: dehydrogenation of naphthenes to aromatics, dehydrocyclization of paraffins, isomerization of paraffins and naphthenes, dealkylation of alkylaromatics, hydrocracking of paraffins to light hydrocarbons, and formation of coke which is deposited on the catalyst. Increased aromatics and gasoline-octane needs have turned attention to the paraffin-dehydrocyclization reaction, which is less favored thermodynamically and kinetically in bifunctional reforming than other aromatization reactions. Considerable leverage exists for increasing desired product yields from aromatization by promoting the dehydrocyclization reaction over the competing hydrocracking reaction while minimizing the formation of coke.

The effectiveness of aromatization catalysts comprising a non-acidic L-zeolite and a platinum-group metal for dehydrocyclization of paraffins is well known in the art. The use of these aromatization catalysts to produce aromatics from paraffinic raffinates as well as naphthas has been disclosed. Commercialization has been slow and is limited in scope in light of special pretreating required to obtain the relatively high selectivity to aromatics that this technology features. Further, such catalysts yield a high proportion of benzene and toluene compared to the more desired xylenes. Thus, there is a particular need for further improvements in selectivity as well as activity and stability of such dehydrocyclization catalysts.

The art discloses reforming with a broad range of catalysts containing large-pore zeolites and Group VIII metals. U.S. Pat. No. 4,104,320 (Bernard et al.) discloses dehydrocyclization with potassium-form L-zeolite charged with one or more dehydrogenating metals of Group VIII and another metal such as rhenium, iridium, tin or germanium. Bernard et al. teach that the other metal preferably is introduced at the same time as platinum or palladium and does not suggest such metals in the framework of the L-zeolite.

U.S. Pat. No. 4,990,710 (Dessau et al.) teaches dehydrogenation to yield aromatics using a tin-modified microporous crystalline silicate. U.S. Pat. No. 5,518,708 (Skeels et al.) teaches a molecular sieve having tin or chromium as framework tetrahedral oxide units, with zeolites Y and L being among the disclosed sieves. The use of such sieves is disclosed generally for a plethora of hydrocarbon-conversion, separation and oxidative combustion processes.

None of the above references discloses aromatization with a catalyst containing a bound nonacidic large-pore molecular sieve containing framework tin and a platinum-group metal component.

SUMMARY OF THE INVENTION

It is an object of the present invention to provide a catalytic system and aromatization process effective for the dehydrocyclization of paraffins and/or olefins with high catalyst selectivity and stability.

This invention is based on the discovery that a bound L-zeolite catalyst containing tin introduced via secondary synthesis and platinum results in substantial yield improvements in an aromatization process.

A broad embodiment of the present invention is an aromatization process, selective for dehydrocyclization of one or both of paraffin and olefin isomers to corresponding aromatic isomers, using a catalyst comprising a bound nonacidic large-pore molecular sieve having a unit empirical formula on an anhydrous basis of $mA:(Sn_wAl_xSi_y)O_2$; where A is at least one exchangeable cation selected from the group consisting of alkali and alkaline earth metals, "m" is the mole fraction of A and varies from about 0.01 to about 0.49, "w" is the mole fraction of tin and varies from about 0.01 to about 0.49, "X" is the mole fraction of aluminum and varies from about 0.01 to about 0.49, and "y" is the mole fraction of silicon and varies from about 0.50 to about 0.98. The tin preferably is introduced into the sieve via secondary synthesis, especially via a solution of a fluoro salt of tin. The molecular sieve is bound using an inorganic-oxide binder which preferably comprises one or both of silica and alumina. The catalyst comprises at least one platinum-group metal component, preferably comprising platinum. Optimally, the molecular sieve comprises potassium-form L-zeolite.

The aromatization process converts paraffins and/or olefins in a hydrocarbon feedstock with high selectivity to obtain an aromatized. Operating conditions comprising low operating pressures, optimally between about 100 and 300 kPa, are used to advantage. Preferably one or more paraffinic and/or olefinic isomers are aromatized to an aromatized product containing one or more corresponding aromatic isomers of the same carbon number in high yield. Heptanes/heptenes and octanes/octenes are efficiently aromatized to toluene and $C_8$ aromatics, respectively. Specific aromatic isomers may be produced by aromatization of individual paraffinic or olefinic isomers, e.g., paraxylene from 2,5-dimethylhexane or 2,5-dimethylhexene.

These as well as other objects and embodiments will become apparent from the detailed description of the invention.

DESCRIPTION OF THE PREFERRED EMBODIMENTS

Figure 1:
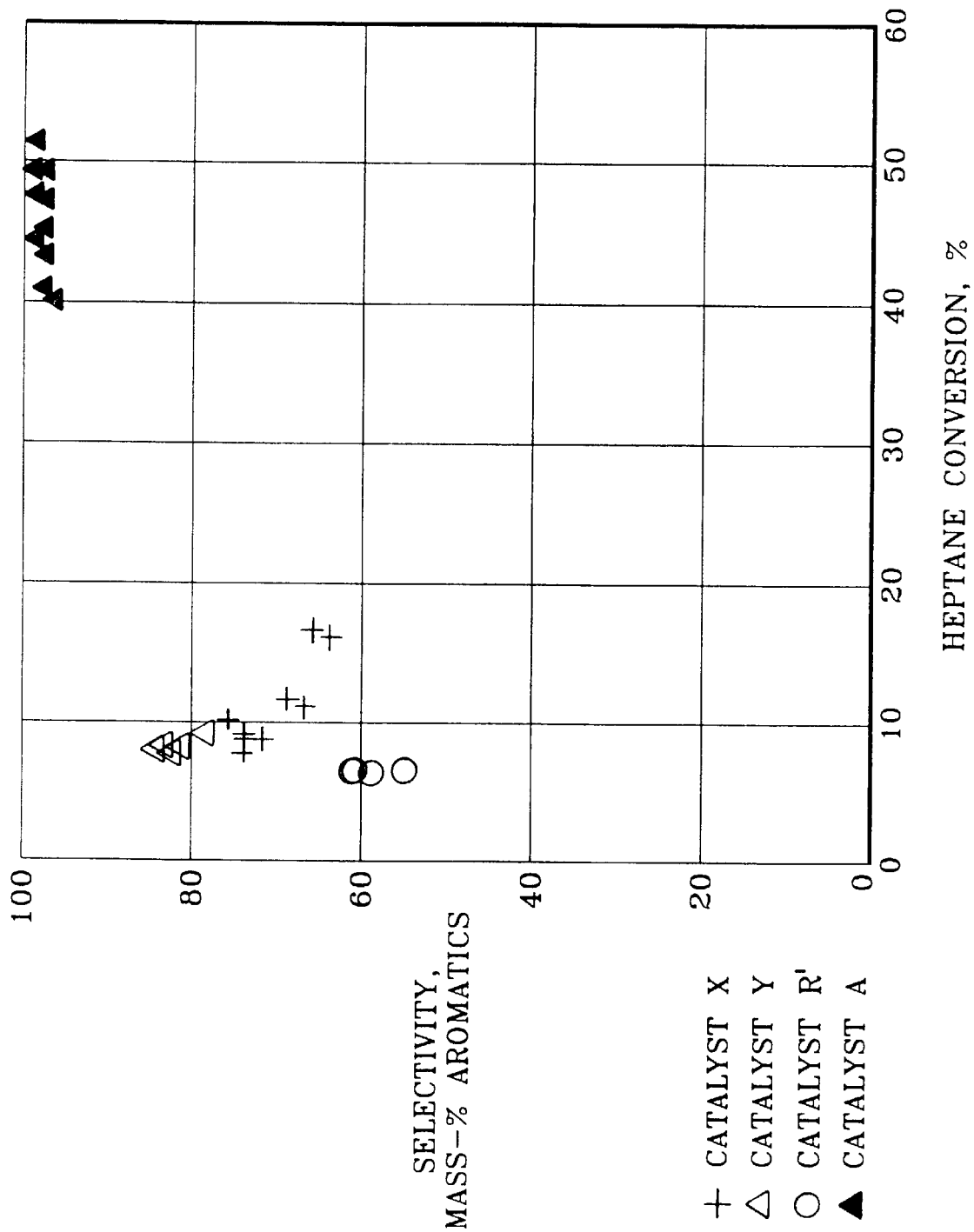
FIG. 1 shows selectivity to toluene as a function of conversion for the processing of heptane using a catalyst of the invention in comparison to catalysts of the known art.

A broad embodiment of the present invention is directed to an aromatization process using a catalyst comprising a platinum-group metal supported on a bound molecular sieve having a unit empirical formula on an anhydrous basis of $mA:(Sn_w Al_x Si_y)O_2$; where A is at least one exchangeable cation selected from the group consisting of alkali and alkaline earth metals, "m" is the mole fraction of A and varies from about 0.01 to about 0.49, "w" is the mole fraction of tin and varies from about 0.01 to about 0.49, "x" is the mole fraction of aluminum and varies from about 0.01 to about 0.49, and "y" is the mole fraction of silicon and varies from about 0.50 to about 0.98. The present aromatization process is particularly selective for dehydrocyclization of paraffins and/or olefins derived from a broad range of feedstocks to selectively yield aromatics having the same number of carbon atoms as the feedstock paraffin and/or olefin.

A hydrocarbon feedstock to the present aromatization process comprises one or both of paraffins and olefins, and may comprise naphthenes and aromatics, preferably boiling within the gasoline range. Feedstocks which may be utilized include straight-run naphthas, natural gasoline, synthetic naphthas, thermal gasoline, catalytically cracked gasoline, partially reformed naphthas or raffinates from extraction of aromatics. The distillation range may be that of a full-range naphtha, having an initial boiling point typically between about 40°–80° C. and a final boiling point between about 160°–210° C., or it may represent a narrower range with a lower final boiling point. Light paraffinic feedstocks having a final boiling point between about 100°–160° C. and containing 60–95 mass-% or more of paraffins, such as naphthas from Middle East crudes, are preferred due to the specific ability of the process to dehydrocyclize paraffins to aromatics. Raffinates from aromatics extraction, containing principally low-value $C_6$–$C_8$ paraffins which can be converted to valuable B-T-X aromatics, are especially preferred feedstocks. Paraffinic and/or olefinic feedstocks of a single carbon-number range can be converted selectively to aromatics of the same carbon-number range, e.g., $C_8$ paraffins or olefins are converted selectively to $C_8$ aromatics using the present aromatization process. The feedstock in some instances may comprise or consist essentially of a single paraffin isomer which is aromatized to a specific aromatic isomer, e.g., a single heptane or octane isomer selected from n-heptane or n-octane or the methylhexanes, dimethylbutanes, methylheptanes, dimethylhexanes, ethylpentane, ethylhexane, or trimethylpentane which are aromatized to toluene, ethylbenzene or one of the xylene isomers. The feedstock also may comprise or consist essentially of a specific olefin isomer or isomers which is aromatized to a specific aromatic isomer, such as a single heptene or octene isomer selected from n-heptene or n-octene or the methylhexenes, dimethylbutenes, methylheptenes, dimethylhexenes, ethylpentene, ethylhexene, or trimethylpentene which are aromatized to toluene, ethylbenzene or one of the xylene isomers.

A suitable alternative feedstock comprises unsaturated hydrocarbons obtained by oligomerization of lighter unsaturates. For example, ethylene, propylene and butylene may be oligomerized individually or in admixture to obtain hexenes, heptenes, octenes and higher olefins which are suitable feedstocks to the present process. A particularly preferred feedstock consists essentially of octenes obtained by oligomerization of butylenes, e.g., specific octene isomers produced by oligomerization of isobutylene.

An untreated hydrocarbon feedstock to the present process may contain small amounts of sulfur compounds, amounting to generally less than 10 parts per million (ppm) on an elemental basis. Preferably the untreated hydrocarbon feedstock has been processed by a conventional pretreating step such as hydrotreating, hydrorefining or hydrodesulfurization to convert such contaminants as sulfurous, nitrogenous and oxygenated compounds to $H_2S$, $NH_3$ and $H_2O$, respectively, which then can be separated from the hydrocarbons by fractionation. This pretreating preferably will employ a catalyst known to the art comprising an inorganic oxide support and metals selected from Groups VIB(IUPAC 6) and VIII(IUPAC 9–10). Alternatively or in addition to the conventional hydrotreating, the pretreating step may comprise contact with sorbents capable of removing sulfurous and other contaminants. These sorbents may include but are not limited to one or more of zinc oxide, iron sponge, high-surface-area sodium, high-surface-area alumina, nickel-on-alumina, activated carbons and molecular sieves. Preferably, the pretreating step will provide the aromatization catalyst with a hydrocarbon feedstock having sulfur levels at least as low as disclosed in the prior art as desirable reforming feedstocks, e.g., 1 ppm to 0.1 ppm (100 ppb); sulfur levels of 0.5 to 0.15 ppm are usual in modern pretreating units.

Optionally, the hydrocarbon feedstock is essentially sulfur-free. Selective aromatization catalysts for aromatization of paraffins are known to be highly sulfur-sensitive, and some benefit may be derived from a sulfur-free feedstock even when utilizing the present active, stable catalyst. Sulfur-free is defined as containing less than 20 parts per billion (ppb), and preferably less than 14 ppb, sulfur. The repeatability of the American National Standard test ASTM D 4045-87 is 20 ppb at a sulfur level of 0.02 ppm (20 ppb), and "sulfur free" according to this test therefore would be defined as less than 20 ppb sulfur. It is believed, however, that one laboratory testing a series of similar samples can detect differences at lower sulfur levels, e.g., 10 mg/ml or 14 ppb sulfur.

Optionally, the hydrocarbon feedstock is processed using a ring-cleavage catalyst, in order to convert naphthenes in the feedstock, with the intermediate from ring cleavage being processed in the present aromatization process. Through the conversion of naphthenes to aliphatics, the selective reactions of the present process are effected on a higher proportion of the feedstock. Ring cleavage is described in, e.g., U.S. Pat. No. 5,463,155, incorporated herein by reference.

The process of the present invention is particularly effective at relatively low operating pressures. Operating conditions in an aromatization zone include a pressure of from about 100 kPa to 1.0 MPa (absolute), with the preferred range being from about 100 to 500 kPa and a pressure of below about 300 kPa being especially preferred. Free hydrogen optionally is supplied to the process in an amount sufficient to correspond to a ratio of from about 0.1 to 10 moles of hydrogen per mole of hydrocarbon feedstock. By "free hydrogen" is meant molecular $H_2$, not combined in hydrocarbons or other compounds. Preferably, the reaction is carried out in the absence of added halogen. The volume of catalyst corresponds to a liquid hourly space velocity of from about 0.5 to 40 $hr^{-1}$. The operating temperature generally is in the range of about 260° to 600° C. Temperature selection is influenced by product objectives, with higher temperatures effecting higher conversion of the feedstock to aromatics. Hydrocarbon types in the feedstock also influence temperature selection, as naphthenes are largely dehydrogenated over the first portion of the aromatization catalyst which the feedstock contacts with a concomitant sharp decline in temperature across the first catalyst bed due to the endothermic heat of reaction. The temperature generally is slowly increased during each period of operation to compensate for inevitable catalyst deactivation.

The aromatization process produces an aromatics-rich effluent stream, with the aromatics content of the $C_5+$ portion of the effluent typically within the range of about 45 to 95 mass-%, and more usually more than about 85 mass-%. The composition of the aromatics depends principally on the feedstock composition and operating conditions, and consists principally of $C_6$–$C_{12}$ aromatics. Benzene, toluene and $C_8$ aromatics are the principal aromatics produced from the preferred light naphtha and raffinate feedstocks.

Paraffins and olefins in the hydrocarbon feedstock are converted selectively in the aromatization zone to the corresponding aromatics, i.e., most of the aromatics produced have the same number of carbon atoms as the paraffins or olefins from which they were converted. Thus hexanes or hexenes yield principally benzene, heptanes or heptenes yield principally toluene, and octanes or octenes yield principally $C_8$ aromatics (xylenes and ethylbenzene). Compared to processes of the known reforming art, a very small proportion of the paraffins or olefins converted yield shorter-chain hydrocarbon fragments and a small proportion of aromatics are dealkylated in the present process. A concomitant of this high selectivity of paraffins and olefins to aromatics is that a very small amount of methane is produced. Usually, when at least about 40 mass-%, preferably at least about 50 mass-%, and more preferably at least about 70 mass-% of the paraffinic hydrocarbons in the feedstock are converted to aromatics or to lighter products, the yield of methane relative to the hydrocarbon feedstock is no more than about 0.5 mass-%, more preferably no more than about 0.2 mass-%, and optimally no more than about 0.1 mass-% in the present process.

It is believed, without thereby limiting the invention, that the reaction proceeds principally by sequential dehydrogenation of paraffins to form olefins, diolefins (dienes) and trienes followed by thermal cyclization. Specific paraffinic and olefinic isomers, representing individual paraffin isomers, thereby are converted to aromatic isomers without rearrangement.

Preferably one or more paraffin and/or olefin isomers thus are aromatized to an aromatized product containing one or more corresponding aromatic isomers of the same carbon number in high yield. Heptanes/heptenes and octanes/ octenes are efficiently aromatized to toluene and $C_8$ aromatics, respectively. The yield of the corresponding aromatic isomers, relative to the aromatized product which comprises the aromatic isomers, other aromatics and hydrocarbons lighter than the feedstock, is at least about 70 mass-%, preferably at least about 80 mass-%, and more preferably at least about 90 mass-%. Dimethylhexanes and dimethylhexenes are aromatized to xylenes containing a relatively low proportion of ethylbenzene. As an example of a specific aromatic isomer which may be produced selectively by aromatization of an individual paraffinic or olefinic isomer, paraxylene is produced selectively from 2,5-dimethylhexane or 2,5-is dimethylhexene.

The aromatization zone comprises one reactor or multiple reactors with provisions known in the art to adjust inlet temperatures to individual reactors. The feed may contact the catalyst system in each of the respective reactors in either upflow, downflow, or radial-flow mode. Since the preferred aromatization process operates at relatively low pressure, the low pressure drop in a radial-flow reactor favors the radial-flow mode. As the predominant dehydrocyclization and dehydrogenation reactions are endothermic, the reactor section generally will comprise two or more reactors with interheating between reactors to compensate for the endothermic heat of reaction and maintain dehydrocyclization conditions.

Using techniques and equipment known in the art, the aromatics-rich effluent usually is passed through a cooling zone to a disengaging zone. In the disengaging zone, typically maintained at about 0° to 65° C., a hydrogen-rich gas is disengaged from a liquid phase. The resultant hydrogen-rich stream can then be recycled through suitable compressing means back to the first aromatization zone. The liquid phase from the disengaging zone is normally withdrawn and processed in a fractionating system in order to adjust the concentration of light hydrocarbons and produce an aromatics-rich effluent product.

The reactor section usually is associated with catalyst-regeneration options known to those of ordinary skill in the art, such as: (1) a semiregenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalyst become deactivated and the catalyst in the isolated reactor is regenerated and reactivated while the other reactors remain on-stream; (3) continuous regeneration of catalyst withdrawn from a moving-bed reactor, with reactivation and substitution of the reactivated catalyst, permitting higher operating severity by maintaining high catalyst activity through regeneration cycles of a few days; or: (4) a hybrid system with semiregenerative and continuous-regeneration provisions in the same unit. The preferred embodiment of the present invention is fixed-bed reactors in a semiregenerative unit.

Optionally, the process comprises an aromatics-rich-product separation zone for separation of aromatics formed in the reaction from unconverted paraffins and olefins and unsaturated hydrocarbons formed in the reaction. The separation zone comprises either solvent extraction, adsorptive separation or a combination of solvent extraction and adsorptive separation in sequence to separate the reformate into a low-octane paraffin fraction and an aromatic-rich fraction. Solvent extraction separates essentially all of the paraffins and olefins, as well as the relatively smaller amounts of naphthenes; from an aromatic concentrate. Adsorptive separation selectively separates classes of paraffin and olefin isomers, depending on the adsorbent and operating conditions, with selected degrees of branching.

Solvent extraction thus produces a concentrated aromatics stream, corresponding approximately to the aromatized product, and a concentrated aliphatic stream containing essentially all of the paraffins and olefins; in contrast, adsorptive separation generally produces a mixed aromatictaliphatic stream and an aliphatic stream containing straight-chain and optionally lower-branched paraffins and olefins.

Solvent extraction suitably comprises contacting the reformate in an extraction zone with an aromatic-extraction solvent which selectively extracts aromatic hydrocarbons. The aromatic hydrocarbons generally are recovered as extract from the solvent phase by one or more distillation steps, and the raffinate from extraction typically is purified by water washing. Solvent extraction normally will recover from about 90 to 100% of the aromatics from the reformate into the extract and reject from about 95 to 100% of the paraffins from the reformate into the raffinate. Solvent compositions are selected from the classes which have high selectivity for aromatic hydrocarbons and are known to those of ordinary skill in the hydrocarbon-processing art. These generally comprise one or more organic compounds containing in their molecule at least one polar group, such as a hydroxyl-, amino-, cyano-, carboxyl-, or nitro-radical, preferably selected from the aliphatic and cyclic alcohols, cyclic monomeric sulfones, glycols and glycol ethers, glycol esters and glycol ether esters. Solvent-extraction conditions are generally well known to those trained in the art and vary depending on the particular aromatic-selective solvent utilized. Further details of solvent extraction as applied to reformate upgrading are as indicated in U.S. Pat. No. 5,294,328, incorporated herein by reference.

Adsorptive separation processes useful in the present invention may be classified by the range of paraffins adsorbed. One type of process separates straight-chain hydrocarbons from all other hydrocarbons, including both branched and cyclic hydrocarbons. Another type of adsorption process separates low-branched paraffins and olefins as well as straight-chain aliphatics from other hydrocarbons, using molecular sieves having a pore diameter of between about 4 and 6 Å; low-branched paraffins and olefins have only one or two tertiary carbons. This type of process typically uses an adsorbent as described in U.S. Pat. No. 4,717,784. The adsorbent used in the present process generally is selected from one or more of AFI, FER, LTA, MEL, MFI, MTT and MTW (IUPAC Commission on Zeolite Nomenclature); and the non-zeolitic molecular sieves of U.S. Pat. Nos. 4,310,440; 4.440,871; and 4,554,143. Especially preferred are isotypic sieves of the AFI structure having large pores (>7 Å), especially AlPO-5 and SAPO-5, in which selective adsorption is not shape selective.

In adsorption using non-shape-selective adsorbents of the AFI structure, higher-octane components such as dimethyl- and trimethyl-paraffins and olefins as well as aromatics are adsorbed from reformates as extract while most of the straight-chain and monomethyl-paraffins and olefins are rejected in the raffinate. This contrasts with the adsorption of straight-chain and low-branched paraffins and olefins using shape-selective adsorbents as described hereinabove. Following adsorption of high-octane components in an AFI adsorbent, a desorbent is employed to displace the paraffinic raffinate from the void spaces of the adsorbent. Desorption of the extract, which is rich in cyclics and multi-branched aliphatics, then is effected with the desorbent. The preferred adsorbent may be employed in the process in the form of a fixed bed in which adsorption of an aromatics concentrate from the aromatics-rich effluent stream is effected followed by displacement of the raffinate and desorption of the extract using a desorbent fluid. Preferably a higher-efficiency countercurrent or simulated moving-bed adsorption system is used, as described, inter alia, in U.S. Pat. Nos. 2,985,589 and 3,274,099. In the latter system, a rotary disc valve as described in U.S. Pat. Nos. 3,040,777 and 3,422,848 is preferably used to distribute input and output streams to and from the adsorption bed.

The separation zone yields an aromatics concentrate and an aliphatic concentrate. The aliphatic concentrate comprises paraffins and olefins unconverted in the aromatization reaction as well as olefins and other unsaturates formed in the reaction. This stream preferably is recycled for further conversion over the aromatization catalyst to increase the yield of aromatics from the present process.

The preferred catalyst of the present invention is an extrudate, usually cylindrical in shape and having a diameter of about 0.8 to 3.2 mm (especially 1.5 to 2.2 mm) and a length to diameter ratio of about 1:1 to 5:1, with 2:1 to 3:1 being especially preferred. Other particle shapes known in the art are within the scope of the invention such as spheres, rods, pills, pellets, tablets or granules; spherical particles may be formed directly or from extrudates by rolling the extrudate particles on a spinning disk.

An essential component of the catalyst particles is a non-acidic large-pore molecular sieve. Suitable molecular sieves generally have a maximum free channel diameter or "pore size" of 6 Å or larger, and preferably have a moderately large pore size of about 7 to 8 Å. Such molecular sieves include, without so limiting the invention, those characterized as AFI, BEA, ERI, FAU, FER, LTL or MWW structure type by the IUPAC Commission on Zeolite Nomenclature; the LTL structure is preferred. It is essential that the preferred L-zeolite be non-acidic, as acidity in the zeolite lowers the selectivity to aromatics of the finished catalyst. In order to be "non-acidic," the zeolite has substantially all of its cationic exchange sites occupied by nonhydrogen species. Preferably the cations "A" occupying the exchangeable cation sites comprise one or more of the alkali and alkaline-earth metals, although other cationic species may be present. An especially preferred nonacidic L-zeolite is potassium-form L-zeolite.

The molecular sieve utilized in the catalyst of the present invention suitably has a unit empirical formula on an anhydrous basis of $mA:(Sn_wAl_xSi_y)O_2$ where A is at least one exchangeable cation selected from the group consisting of alkali and alkaline earth metals, "m" is the mole fraction of A and varies from about 0.01 to about 0.49, "w" is the mole fraction of tin and varies from about 0.01 to about 0.49, "x" is the mole fraction of aluminum and varies from about 0.01 to about 0.49 and "y" is the mole fraction of silicon and varies from about 0.50 to about 0.98.

The molecular sieves are conveniently prepared by the technique disclosed in U.S. Pat. No. 5,518,708 which teachings are incorporated by reference. Generally, the process involves contacting a crystalline zeolite having a molar $SiO_2/Al_2O_3$ ratio of at least 2 with an effective amount of a fluoro salt of tin, preferably in an amount of at least 0.0075 moles per 100 grams of zeolite starting material, the fluoro salt preferably being in the form of an aqueous solution or slurry which is contacted with the zeolite either incrementally or continuously at a slow rate (optionally in the presence of a buffer) whereby framework aluminum atoms of the zeolite are removed and replaced by tin atoms while retaining at least 80 percent and more preferably at least 90 percent of the crystal structure of the starting zeolite.

The fluoro salt preferably is provided as an aqueous solution or slurry, but solutions or slurries employing alcohols or other organic solvents may be suitable alternatives. An effective amount of fluoro salt is that amount which provides sufficient fluoride and tin for the process and the desired amount of tin in the final molecular sieve product. Solutions having fluoro salt concentrations of between about $10^{-3}$ moles per liter of solution and up to saturation of the solution can be employed, but preferably concentrations of between about 0.5 and about 1.0 moles per liter of solution are used. The minimum value for the amount of fluoro salt to be added is usually at least equivalent to the minimum mole fraction of aluminum to be removed from the zeolite.

The solution or slurry is maintained at an effective pH such that, under effective process conditions, a monomeric species of the tin is present in the reaction solution and the pH is high enough to avoid undue destructive acidic attack on the particular zeolite. The effective pH value generally is greater than 1, preferably greater than 3 and more preferably in the range of about 3 to about 7. Crystal degradation of many zeolites is found to be unduly severe at pH values below about 3, whereas insertion of the tin may be slow from a practical standpoint as a result of the solubility of tin at a pH of 7 and above.

The fluoro salt used as the aluminum extractant and as the source of tin can be any of the fluoro salts having the general formula:

$$A_{2/b}SnF_6 \text{ or } A_{2/b}SnF_4$$

where "A" is a metallic or non-metallic cation having a valence "b" including alkylammonium, $H^+$, $NH_4^+$, $Mg^{++}$, $Li^+$, $Na^+$, $K^+$, $Ba^{++}$, $Cd^{++}$, $Cu^{++}$, $Ca^{++}$, $Cs^+$, $Fe^{++}$, $Co^{++}$, $Pb^{++}$, $Mn^{++}$, $Rb^+$, $Ag^+$, $Sr^{++}$, $Tl^+$ and $Zn^{++}$. The ammonium and hydronium cation forms of the fluoro salt are generally preferred because of their solubility in water and also because these cations form water soluble by-product salts upon reaction with the zeolite, e.g., $(NH_4)_3AlF_6$ and/or $(NH_4)_2AlF_5$. Other salts which may be used include a combination of salts of $SnF_2$ and $^3/_2(NH_4HF_2)$ or $SnF_4$ and $NH_4HF_2$. Preferred fluoro salts are $NH_4SnF_3$; $SnF_2 \cdot ^3/_2 (NH_4HF_2)$ and $SnF_4 \cdot NH_4HF_2$.

The selection of a fluoro salt or desirability of buffering the reaction system will in large part depend on the selection of the particular starting zeolite, since zeolites have varying tolerances to acid and base media. The optional buffering may be effected in a manner as generally heretofore employed in the art using buffering salts such as ammonium acetate or an inert solid, such as clays or aluminas, to react with excess acid or base.

The preferred effective reaction temperature is between about 10° C. and about 99° C., preferably between about 20° and 95° C., but temperatures of 125° C. or higher and as low as 0° C. may be employed in some cases. Reaction temperature and reagent concentrations are optimized with respect to the zeolite starting material to provide adequate time for insertion of framework tin consistent with practical commercial considerations. Generally more highly siliceous zeolites enable higher permissible reaction temperatures and lower pH conditions.

In specifying the proportions of the zeolite starting materials or adsorption properties of the zeolite product and the like herein, the "anhydrous state" of the zeolite will be intended unless otherwise stated. The term "anhydrous state" is employed herein to refer to a material substantially devoid of both physically adsorbed and chemically adsorbed such as is typically obtained by heating the zeolite in dry air at about 450° C. for about 4 hours.

It usually is necessary to composite the L-zeolite with a binder in order to provide a convenient form for use in the catalyst particles of the present invention. The art teaches the suitability of a variety of refractory inorganic oxide binders. One or more of silica, alumina or magnesia are preferred binder materials of the present invention. One or both of amorphous silica and alumina are especially preferred. In one embodiment, excellent results are obtained when using a synthetic white silica powder precipitated as ultra-fine spherical particles from a water solution. A silica binder preferably is nonacidic, contains less than 0.3 mass-% sulfate salts, and has a BET surface area of from about 120 to 160 m²/g.

The L-zeolite and binder may be composited to form particle shapes known to those skilled in the art such as spheres, extrudates, rods, pills, pellets, tablets or granules. Spherical particles may be formed directly by the oil-drop method as disclosed hereinbelow or from extrudates by rolling extrudate particles on a spinning disk.

In one method of forming the preferred extrudates, potassium-form L-zeolite and amorphous silica are commingled as a uniform powder blend prior to introduction of a peptizing agent. An aqueous solution comprising one or both of KOH and NaOH is added to form an extrudable dough. The dough preferably will have a moisture content of from 30 to 50 mass-% in order to form extrudates having acceptable integrity to withstand direct calcination. The resulting dough is extruded through a suitably shaped and sized die to form extrudate particles, which are dried and calcined generally by known methods. Preferably, extrudates are subjected directly to calcination without an intermediate drying step in order to encapsulate potassium ions and preserve basicity. The calcination of the extrudates is effected in an oxygen-containing atmosphere at a temperature of from about 260° to 650° C. for a period of about 0.5 to 2 hours.

An alternative alumina-bound form of the present catalyst support is a sphere. Alumina-bound spheres may be continuously manufactured by the well known oil-drop method which comprises: forming an alumina hydrosol by any of the techniques taught in the art and preferably by reacting aluminum metal with hydrochloric acid; combining the resulting hydrosol with the zeolite and a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and an ammoniacal solution to further improve their physical characteristics. The resulting aged and gelled particles are then washed and dried at a relatively low temperature of about 150° to about 205° C. and subjected to a calcination procedure at a temperature of about 450° to about 700° C. for a period of about 1 to about 20 hours. This treatment effects conversion of the alumina hydrogel to the corresponding crystalline gamma-alumina. U.S. Pat. No. 2,620,314 provides for additional details and is incorporated therein by reference thereto.

An aromatization-catalyst support may incorporate other porous, adsorptive, high-surface-area materials. Within the scope of the present invention are refractory supports containing one or more of: (1) refractory inorganic oxides such as alumina, silica, titania, magnesia, zirconia, chromia, thoria, boria or mixtures thereof, (2) synthetically prepared or naturally occurring clays and silicates; which may be acid-treated; (3) non-zeolitic molecular sieves, such as the aluminophosphates or silicoaluminophosphates of U.S. Pat. Nos. 4,310,440, 4,440,871 and 4,554,143, (4) spinels such as $MgAl_2O_4$, $FeAl_2O_4$, $ZnAl_2O_4$; and (5) combinations of materials from one or more of these groups.

An alkali-metal component is a highly preferred constituent of the aromatization catalyst particles. One or more of the alkali metals, including lithium, sodium, potassium, rubidium, cesium and mixtures thereof, may be used, with potassium being preferred. The alkali metal optimally will occupy essentially all of the cationic exchangeable sites of the non-acidic L-zeolite as described hereinabove.

Of the Group VIII platinum-group noble metals, i.e., platinum, palladium, rhodium, ruthenium, osmium and iridium, platinum is preferred. Mixtures of platinum-group metals also are within the scope of this invention, but it is preferred that the platinum-group metal component consists essentially of a platinum component. The platinum-group metal component may exist within the final catalytic composite as a compound such as an oxide, sulfide, halide, or oxyhalide, in chemical combination with one or more of the other ingredients of the composite, or as an elemental metal. Best results are obtained when substantially all of the metals are present in the elemental state. The platinum-group metal component may be present in the final catalyst composite in any amount which is catalytically effective, but relatively small amounts are preferred. The uniformly distributed platinum-group metals generally will comprise from about 0.01 to 5 mass-% of the final catalyst, and preferably about 0.05 to 2 mass-%, calculated on an elemental basis.

The ratio of tin to platinum in the finished catalyst affects catalyst performance, particularly conversion of paraffinic hydrocarbons at a given set of operating conditions. The Sn/Pt mass ratio preferably is above about 1.5, and more preferably at least about 2; in some cases, a ratio of 3 or more is advantageous.

The platinum-group metal component may be incorporated in the porous carrier material in any suitable manner, such as coprecipitation, ion-exchange or impregnation. Platinum is the preferred uniformly distributed metal, and optimally is incorporated into the catalyst utilizing a soluble, decomposable compound to impregnate the carrier material in a relatively uniform manner. For example, platinum may be added to the support by commingling the latter with an aqueous solution of chloroplatinic acid, ammonium chloroplatinate, bromoplatinic acid, platinum trichloride, platinum tetrachloride hydrate, platinum dichlorocarbonyl dichloride, tetraamine platinum chloride, tetraamine platinum hydroxide, dinitrodiaminoplatinum, sodium tetranitroplatinate (II), platinum acetylacetonate and the like. In addition, it is generally preferred to impregnate the carrier material after it has been calcined in order to minimize the risk of loss of the valuable platinum-group metal.

It is within the scope of the present invention that the catalyst may contain other metal components known to modify the effect of the platinum-group-metal component. Such metal modifiers may include but are not limited to rhenium, gallium, manganese, zinc, uranium, dysprosium, thallium and mixtures thereof. Catalytically effective amounts of such metal modifiers may be incorporated into the catalyst by any means known in the art. Generally an optional metal modifier is present in a concentration of from about 0.01 to 5 mass-% of the finished catalyst on an elemental basis. The catalyst preferably does not contain such metal modifiers, i.e., the metal component consists essentially of a platinum-group metal component and tin introduced via secondary synthesis.

The aromatization catalyst may contain a halogen component, although the catalyst preferably has the essential absence of halogen. An optional halogen component may be either fluorine, chlorine, bromine or iodine or mixtures thereof with chlorine being preferred. Considering the nonacidic nature of the support, such halogen usually is incorporated into the catalyst only in association with the incorporation of a metal component. An optional halogen component is generally present in a combined state with the inorganic-oxide support, and preferably is well distributed throughout the catalyst and may comprise from more than 0.2 to about 15 mass-% calculated on an elemental basis, of the final catalyst.

The final aromatization catalyst generally is dried at a temperature of from about 100° to 320° C. for about 0.5 to 24 hours, followed by oxidation at a temperature of about 300° to 550° C. (preferably above about 350° C.) in an air atmosphere for 0.5 to 10 hours. Preferably the oxidized catalyst is subjected to a substantially water-free reduction step at a temperature of about 300° to 550° C. (preferably above about 350° C.) for 0.5 to 10 hours or more. The reduction step may be performed in-situ as part of the plant startup if a dry atmosphere is maintained. Further details of the preparation and activation of embodiments of the present aromatization catalyst are disclosed, e.g., in U.S. Pat. No. 4,619,906 (Lambert et al.) and U.S. Pat. No. 4,882,762 (Ellig et al.), which are incorporated into this specification by reference thereto. An alternative embodiment comprises a physical mixture of the above nonacidic catalyst particles with acidic catalyst particles comprising one or more inorganic oxides and preferably having the absence of a platinum-group metal. The present catalyst has been found to be surprisingly selective and stable, in comparison to catalysts of the prior art, in dehydrocyclizing paraffinic feedstocks to achieve high yields of aromatics.

An optional embodiment of the present invention is aromatization of the hydrocarbon feedstock with a physical mixture of the aromatization catalyst and a sulfur sorbent. The mixture is contained either in a fixed-bed reactor or in a moving-bed reactor whereby catalyst may be continuously withdrawn and added. The sulfur sorbent should not only be effective for removal of small amounts of sulfur compounds from hydrocarbon streams at aromatization-catalyst operating conditions, but also be compatible with the aromatization catalyst in order to maintain the activity of the catalyst. The sulfur sorbent comprises a metal oxide, preferably selected from oxides of the metals having an atomic number between 19 and 30 inclusive; these metals, particularly potassium, calcium, vanadium, manganese, nickel, copper and zinc are known to be effective for sulfur removal in various circumstances. The sorbent optimally comprises a manganese component. Manganese oxide has been found to provide reforming catalyst protection superior to the zinc oxide of the prior at, it is believed, due to possible zinc contamination of associated reforming catalyst. The manganese oxides include MnO, $Mn_3O_4$, $Mn_2O_3$, $MnO_3$, and $Mn_2O_7$. The preferred manganese oxide is MnO (manganous oxide). The manganese component may be composited with a suitable binder such as clays, graphite, or inorganic oxides including one or more of alumina, silica, zirconia, magnesia, chromia or boria in order to provide a second particle for the physical mixture of the present catalyst system. Preferably, the manganese component is unbound and consists essentially of manganese oxide. Even more preferably the manganese component consists essentially of MnO, which has demonstrated excellent results for sulfur removal and has shown adequate particle strength without a binder for the second particle of the present invention.

EXAMPLES

The following examples are presented to illustrate certain specific embodiments of the present invention in comparison to the known art. These examples should not be construed to limit the scope of the invention as set forth in the claims.

The examples illustrate the effect especially on aromatization selectivity of utilizing catalyst as disclosed in the present invention.

Example I

Ammonium-exchanged zeolite L, $NH_4^+$ zeolite L, was slurried in distilled water to and heated to 75° C. A solution containing $SnF_4$ and $NH_4HF_2$ in distilled water was added incrementally over a period of 10 minutes to the zeolite. Following the addition of the tin solution, the slurry was digested over a one-hour period. The product was filtered and washed free of soluble fluoride. The solid product was yellow and showed the characteristic crystal structure of zeolite L as indicated by X-ray powder diffraction.

The $NH_4$-Sn-zeolite L solid was slurried in distilled water, and the slurry was stirred and heated to 75° C. KCl was added and the mixture was allowed to react for 1–1½ hours, filtered, and the filtrate was washed with deionized water. This procedure was repeated five times to yield K-Sn-zeolite L.

Platinum was impregnated as tetraamineplatinum chloride (TAPC) by evaporative impregnation onto the zeolite powder. The impregnated powders then were oxidized for 0.5 hour at 200° C. and 2 hours at 350° C. Reduction was effected with dilute hydrogen in situ in the microreactor used for catalyst testing for 1 hour at 550° C.

The finished catalyst, designated as Catalyst A, had the following metals contents on an elemental basis in mass-%:

| | |
|---|---|
| Platinum | 0.29 |
| Tin | 0.62 |

Additional catalysts of the invention were prepared as described above with differing platinum and tin contents. The catalysts had the following designations and metals contents in mass-%:

| Catalyst | Platinum | Tin |
|---|---|---|
| A | 0.29 | 0.62 |
| B | 0.34 | 0.63 |
| C | 0.35 | 0.48 |
| D | 0.50 | 0.34 |
| E | 0.21 | 0.70 |
| F | 1.2 | 0.62 |
| G | 1.2 | 2.1 |

Example II

Two zeolitic catalysts as known in the art, not of the invention and containing a single Group VIII (IUPAC 8-10) noble metal component consisting essentially of platinum, were used as a control or reference and designated as Catalysts R and R'. The platinum was impregnated as tetraamineplatinum chloride (TAPC) by evaporative impregnation onto a 1.6 mm extruded support comprising about 85 mass-% potassium-form L-zeolite and 15 mass-% silica.

Catalyst R was dried at 175° C. and 270° C., oxidized at 425° C. in air for 1 hour, and reduced with dry hydrogen at 350° C. for 1.5 hours, and contained 0.86 mass-% Pt.

Catalyst R' was finished by oxidation at 150° C. in air for 3 hours and reduction with dry hydrogen at 350° C. for 1.5 hours, and contained 0.75 mass-% Pt.

Example III

A bifunctional spherical catalyst of the known art was prepared for additional comparisons with catalysts of the invention. Tin was incorporated into alumina sol, and the sol was oil-dropped to form 1.6-mm spheres which were steamed to dryness and calcined at about 650° C. The resulting calcined composite was impregnated with chloroplatinic acid in HCl and finished by drying and dxychlorination at 525° C. and reduction with pure hydrogen at 565° C. The finished control catalyst was designated Catalyst X and had the following metals concentrations on an elemental basis in mass-%:

| | |
|---|---|
| Platinum | 0.38 |
| Tin | 0.3 |

Two additional spherical control catalysts of the known art Y and Y' were prepared in a manner similar to Catalyst X, except that nonacidity was conferred by the incorporation respectively of lithium and potassium. Catalyst Y was prepared in the manner disclosed in U.S. Pat. No. 4,716,143, conferring nonacidity on the catalyst by adding $LiNO_3$ to the impregnation solution; the finished catalyst contained 0.38 mass-% Pt and 0.5 mass-% Sn on an elemental basis. Catalyst Y' was prepared by successive impregnation of platinum and potassium, with an intermediate oxidation step; the finished catalyst contained 0.75 mass-% Pt and 0.5 mass-% Sn.

Example IV

Catalyst A was tested in a microreactor for reforming performance in comparison to the catalysts of the known art described in Examples II and III. The feedstock used in the test was normal heptane, greatly diluted to a 1.9% concentration in nitrogen containing hydrogen at a 1.1 molar hydrogen/heptane ratio to sharpen the distinction in comparative test results. The tests were carried out at a pressure of 1 atmosphere absolute, 500° C., and 2.2 weight hourly space velocity (WHSV).

Figure 2:
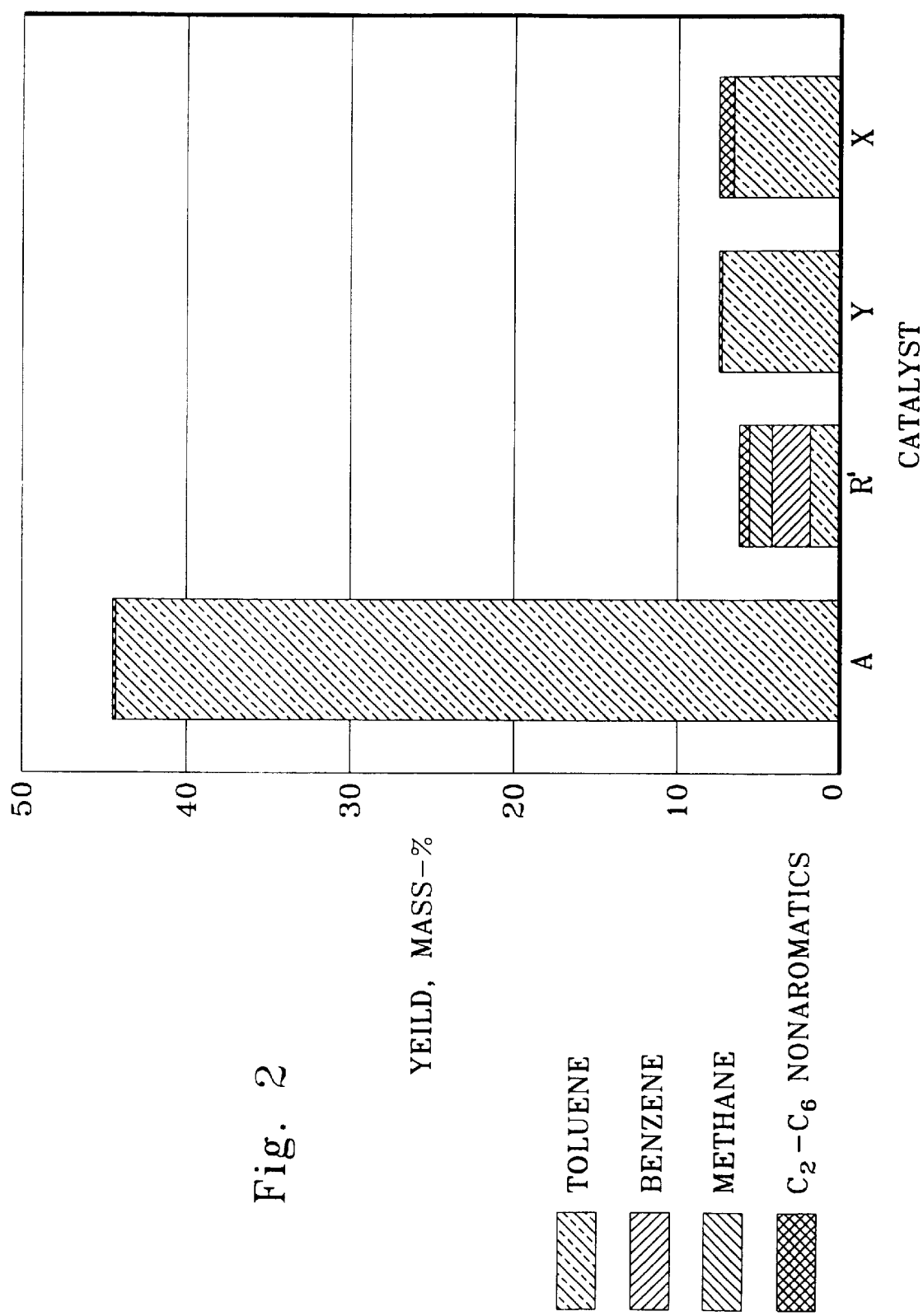
FIG. 2 is a bar chart showing yield patterns for the processing of heptane using a catalyst of the invention and catalysts of the art.

The results of the comparative tests on a dilute heptane feed are shown in FIGS. 1 and 2. FIG. 1 is a plot of selectivity to aromatics in relation to conversion. Conversion is defined as the proportion of heptane converted to cyclics+lighter hydrocarbons. Catalyst A showed significantly higher selectivity to aromatics and conversion than the Catalysts R, X and Y of the known art.

FIG. 2 is a bar chart showing the major product groups from the reforming test described above for Catalyst A and control catalysts. This chart emphasizes the conversion and yield advantage of Catalyst A, particularly over Catalyst R which is a counterpart of Catalyst A without framework tin.

Methane yields from the comparative reforming tests on Catalysts A and R were determined. Catalyst A of the invention yielded 0.06 mass-% methane, while reference Catalyst R yielded 1.36 mass-% methane.

Example V

The range of catalysts (A,B,C,D,E,F,G) of the invention disclosed in Example I were tested for reforming performance in comparison to nonacidic lithiated platinum-tin-on-alumina Catalyst Y of the known art, which was the best-performing of the control catalysts according to Example IV.

The feedstock and operating conditions used in the test were the same as described in Example IV: normal heptane, greatly diluted to a 1.9% concentration in nitrogen containing hydrogen at a 1.1 molar hydrogen/heptane ratio to sharpen the distinction in comparative test results, processed at a pressure of 1 atmosphere absolute, 500° C., and 2.2 weight hourly space velocity (WHSV).

Figure 3:
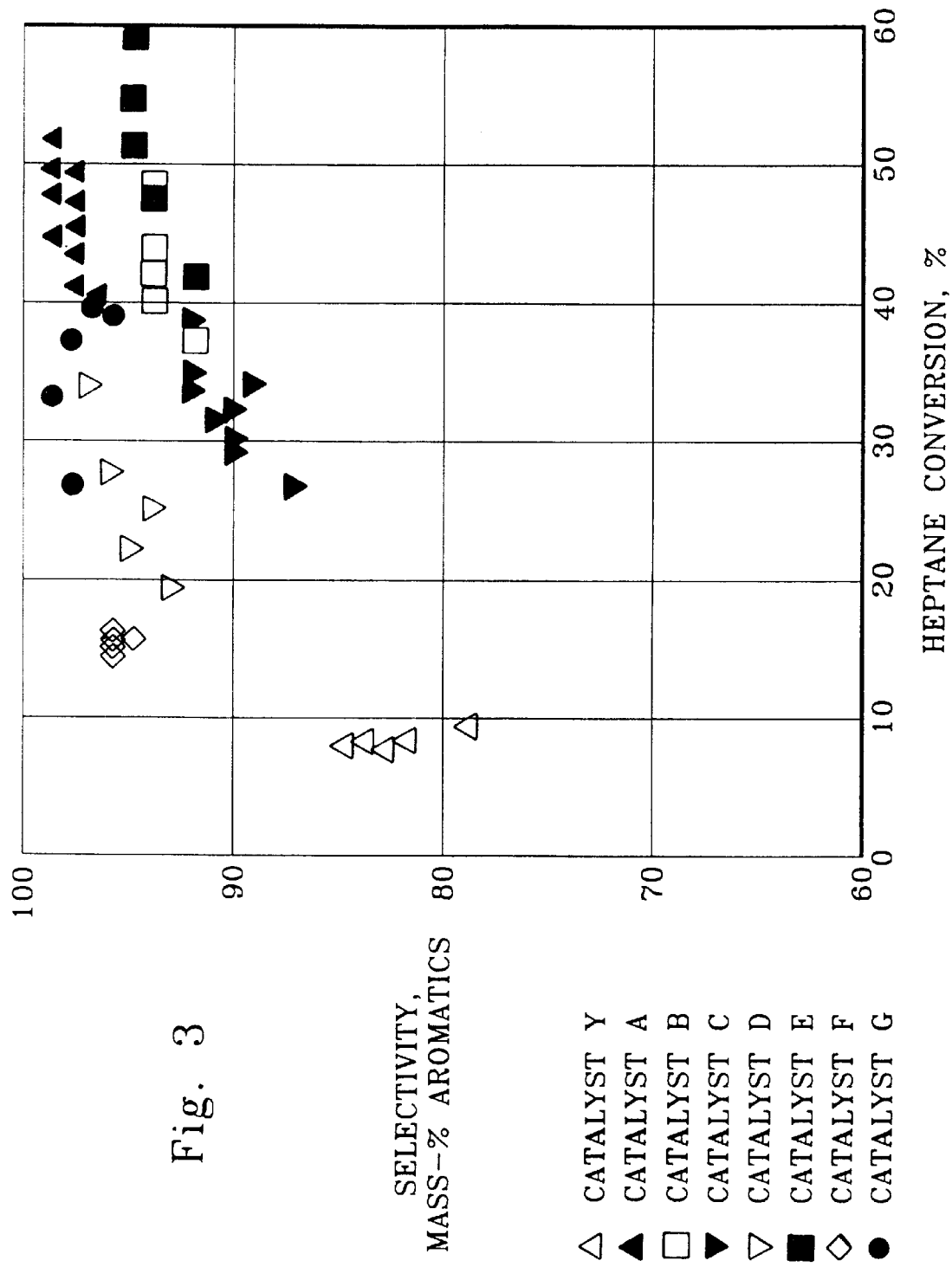
FIG. 3 shows selectivity to toluene as a function of conversion for the processing of heptane using alternative catalysts of the invention in comparison to a reference catalyst of the art.

The results of the comparative tests on a dilute heptane feed are shown in FIG. 3. All of the catalysts of the invention showed significantly higher selectivity to aromatics products at higher conversion than Catalyst Y of the art.

Figure 4:
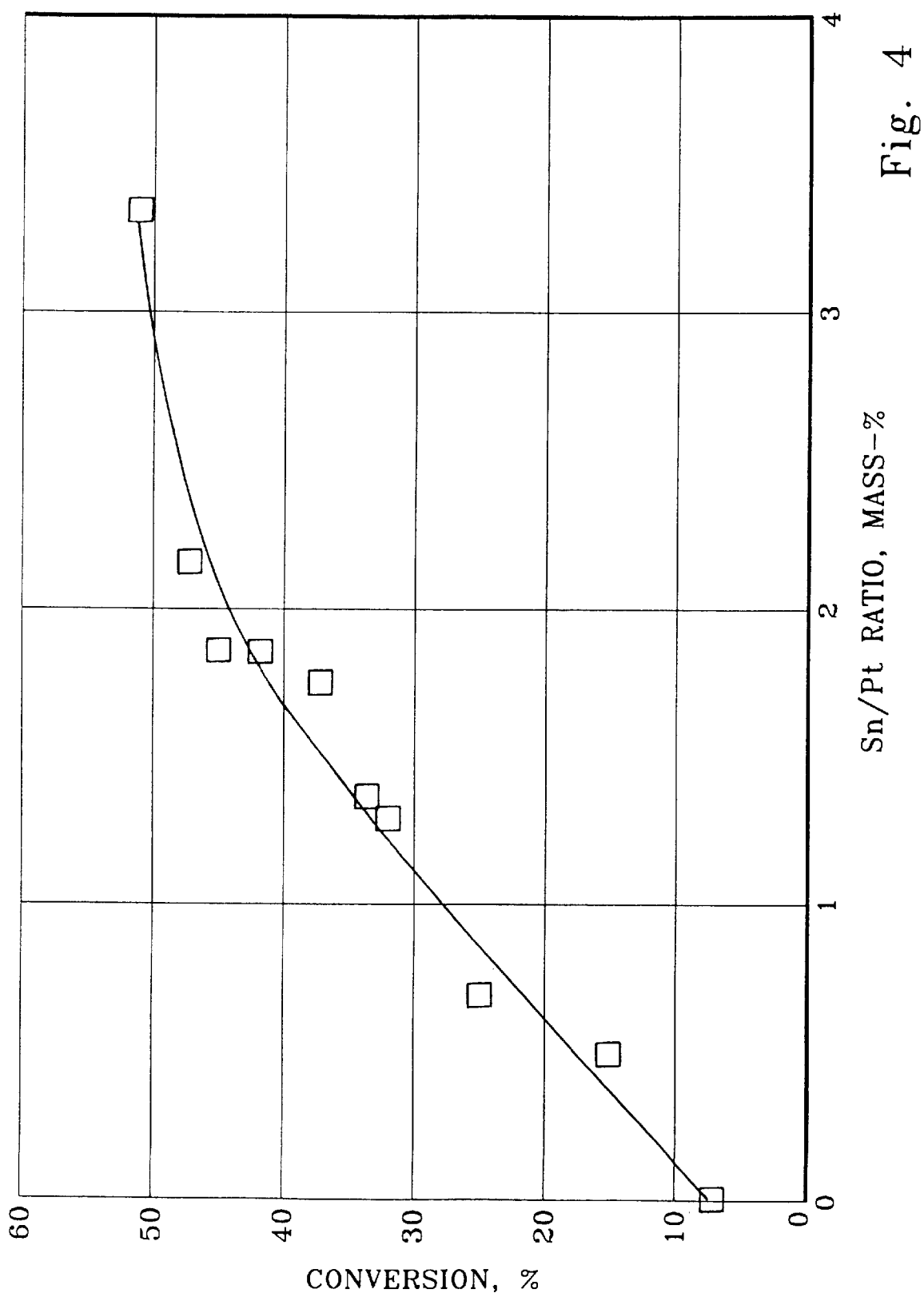
FIG. 4 shows conversion of heptane as a function of the Sn/Pt ratio of the catalyst.

Average conversion is compared as a function of Sn/Pt mass ratio for the Example I catalysts of the invention in FIG. 4. Higher conversion is obtained with higher Sn/Pt ratios, leveling off above a Sn/Pt ratio of 2.

Example VI

Catalyst H was prepared by silica binding of the zeolite powder prepared as described in Example 1, followed by extrusion to provide catalyst particles. Platinum was impregnated as tetraamineplatinum chloride (TAPC) by evaporative impregnation onto the extrudates prepared from the bound zeolite. The catalyst particles then were finished by oxidation for 0.5 hour at 200° C. and 2 hours at 350° C. and reduced with hydrogen for 2 hours at 650° C.

Example VII

The finished Catalyst H was tested in a pilot plant for reforming performance in comparison to reference Catalyst X. The feedstock used in the test was a blend of normal heptane and orthoxylene in a 90/10 mass ratio. The tests were carried out at a pressure of 200 kPa, 6.2 WHSV, and 1.1 molar hydrogen/hydrocarbon ratio. Temperature was varied in 10° C. increments from 474° to 524° C.

Figure 5:
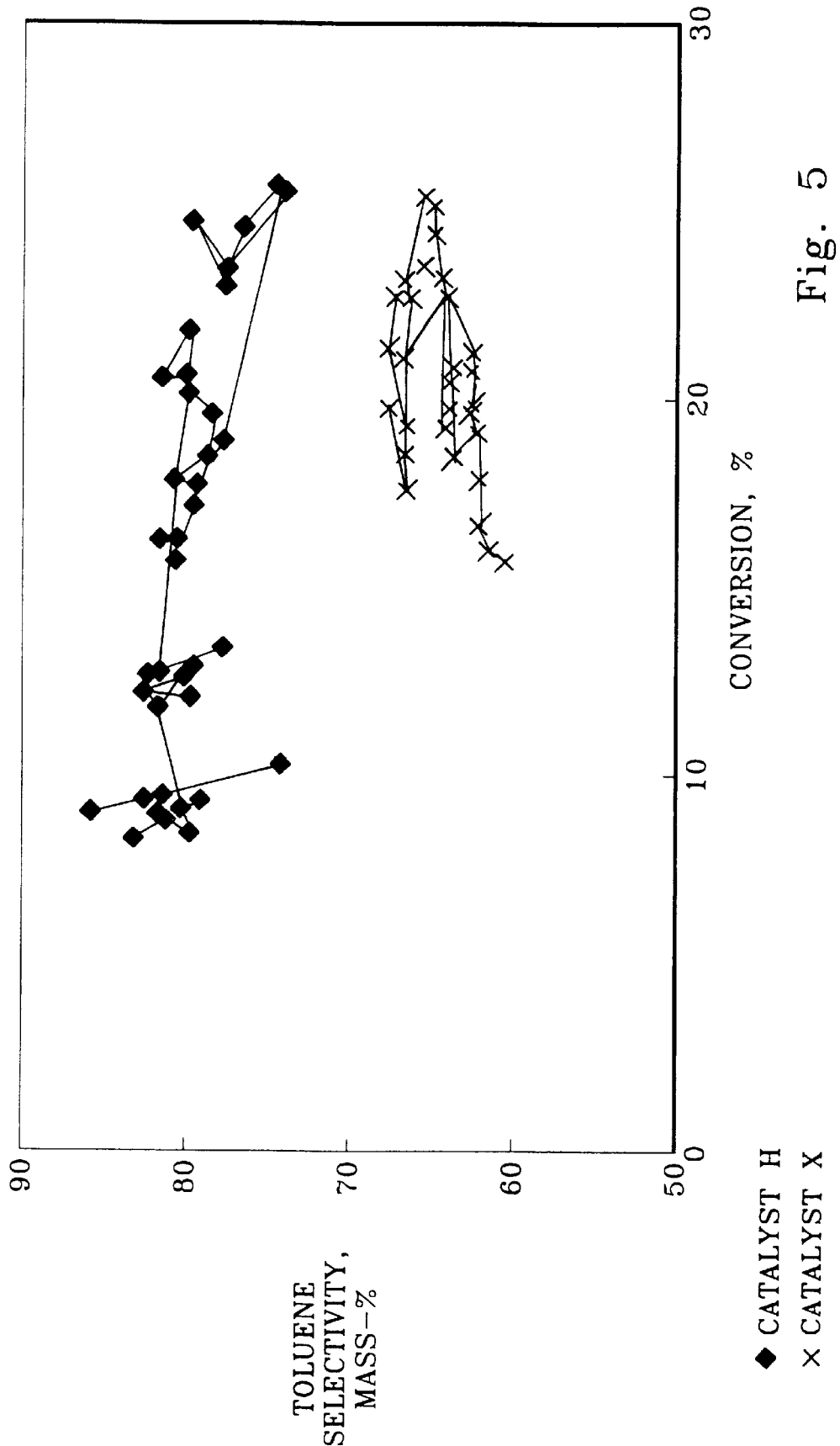
FIG. 5 shows pilot-plant results showing toluene yields at varying temperatures using a catalyst of the invention in comparison to a catalyst of the art.

The results of the comparative pilot-plant tests are shown in FIG. 5 as a plot of selectivity to toluene in relation to conversion, again defined as the proportion of heptane converted to cyclics+lighter hydrocarbons. The scatter in the data result principally from changes in catalyst activity during the life of the test. Catalyst H showed significantly higher selectivity than did Catalyst X of the known art.

Example VIII

Catalyst A was microreactor-tested with a 2,5-dimethylhexane feedstock in comparison to the catalysts of the known art described in Examples II and III. The is paraffinic feedstock contained about 97.5% 2,5-dimethylhexane The feedstock was greatly diluted to a 1.1% concentration in nitrogen containing hydrogen at a 1.8 molar hydrogen/heptane ratio to sharpen the distinction in comparative test results. The tests were carried out at a pressure of 1 atmosphere absolute, 500° C., and 1.5 weight hourly space velocity (WHSV).

Figure 6:
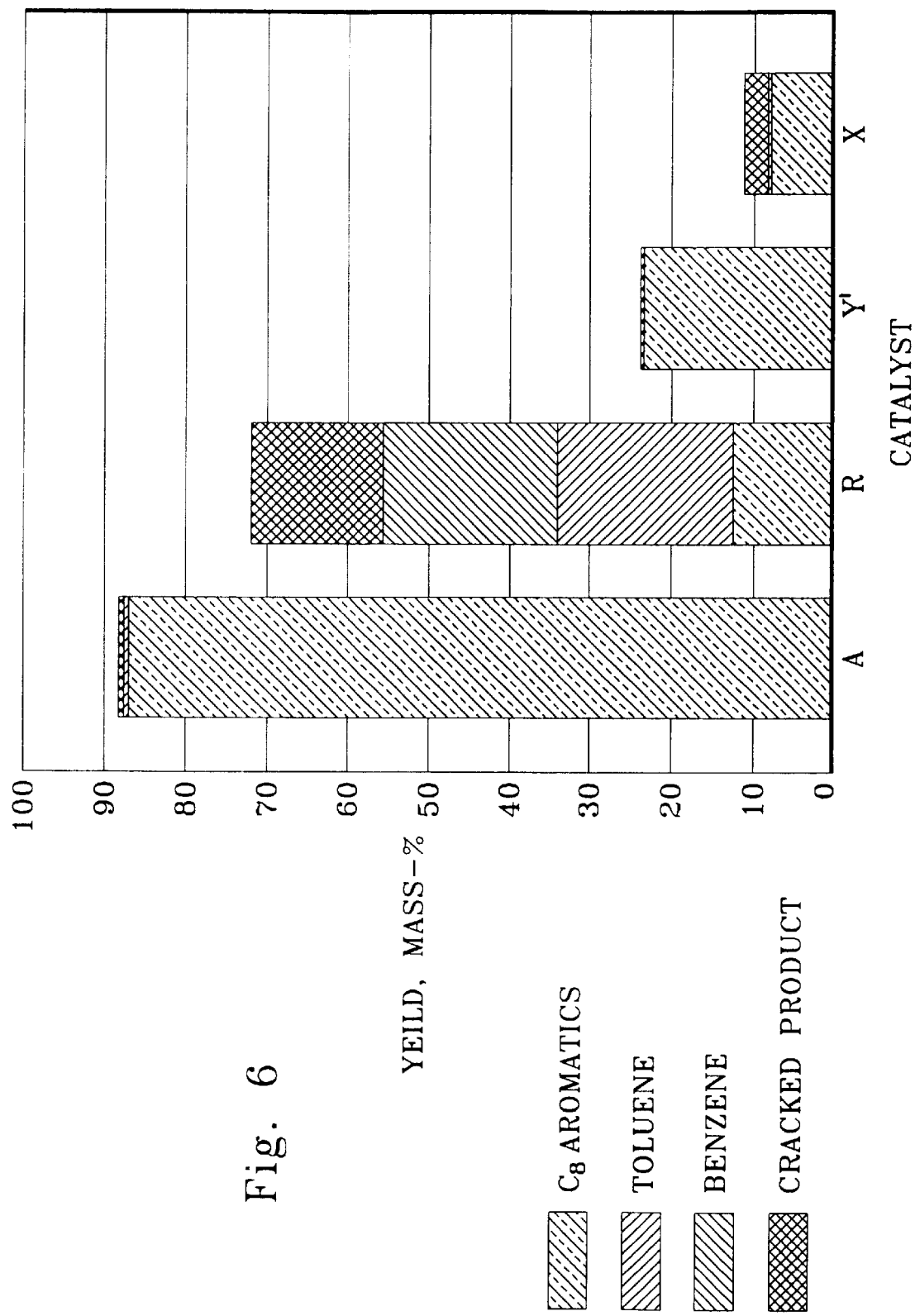
FIG. 6 is a bar chart showing yield patterns for the processing of 2,5-dimethylhexane using a catalyst of the invention and catalysts of the art.
Figure 7:
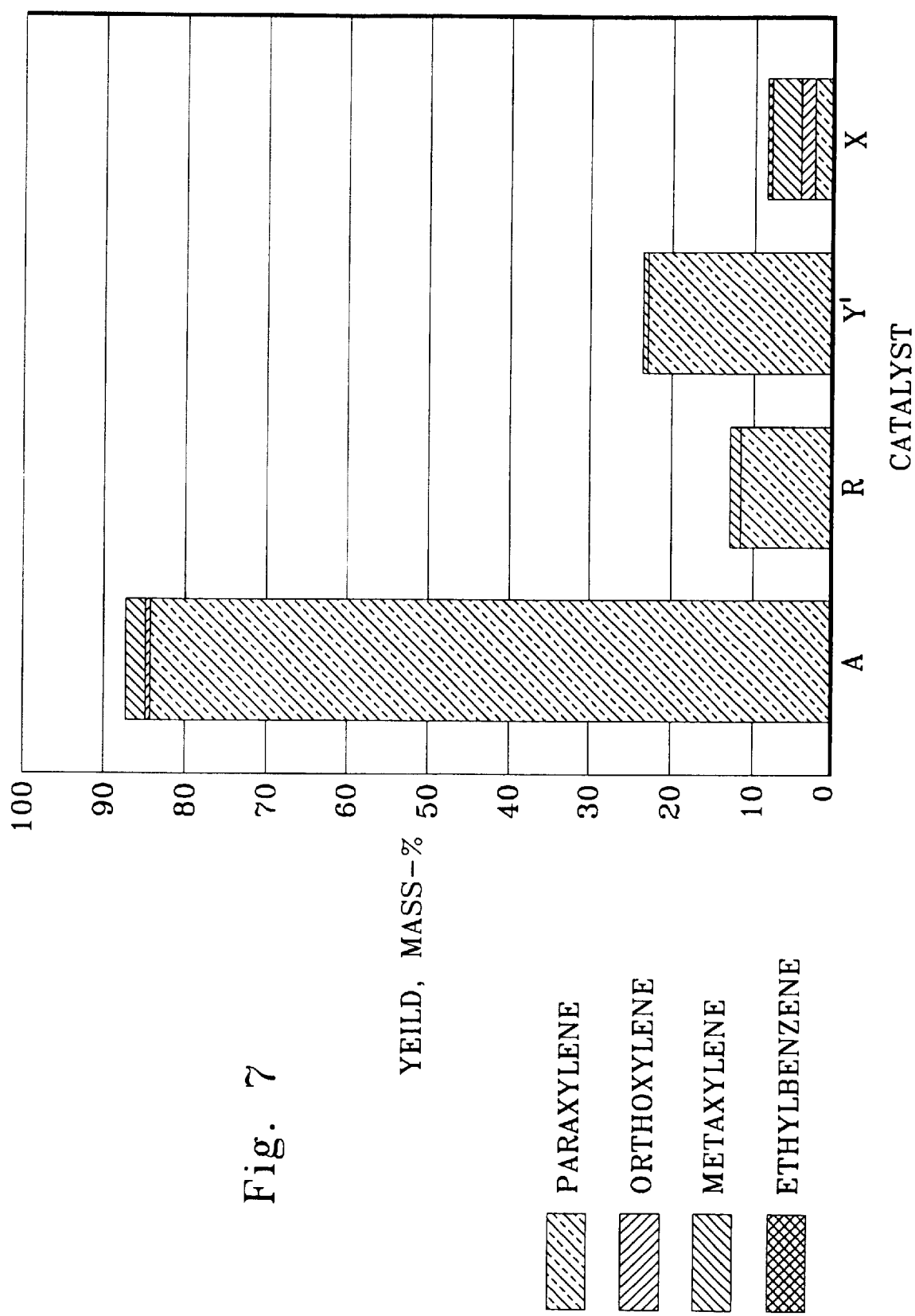
FIG. 7 is a bar chart showing $C_8$-aromatic isomer distribution for the processing of 2,5-dimethylhexane using a catalyst of the invention and catalysts of the art.

The results of the comparative tests on a dilute 2,5-dimethylhexane feed are shown in FIGS. 6 and 7. FIG. 6 is a bar chart showing the major product groups from the reforming test described above for Catalyst A and control catalysts. This chart emphasizes the conversion and yield advantage of Catalyst A. The selectivity to $C_8$ aromatics is about 87 mass-%, a selectivity unknown in the art.

The ratio of $C_8$ aromatic isomers produced by the different catalysts is shown in FIG. 7. Catalyst A yields only about 3% isomers other than para-xylene, with a resulting para-xylene yield from the paraffin feedstock of about 84 mass-%. The $C_8$ aromatic isomers other than paraxylene may be derived principally from the impurities in the 2,5-dimethylhexane feed.

The foregoing description sets forth essential and preferred features of this invention which can be adapted in the context of a variety of applications and arrangements without departing from the scope and spirit of the claims hereafter presented. There are many other possible embodiments and variants, as can be appreciated by the skilled routineer, which are within the spirit of the invention as claimed.

We claim:

1. A process for the aromatization of one or more paraffinic isomers in a hydrocarbon feedstock comprising contacting the feedstock with an aromatization catalyst in an aromatization zone at aromatization conditions to obtain an aromatics-rich effluent containing an aromatized product comprising at least 70 mass-% of one or more corresponding aromatic isomers having the same number of carbon atoms as the paraffinic hydrocarbon isomers, the catalyst comprising:

(a) a nonacidic L-zeolite having a unit empirical formula on an anhydrous basis of $mA:(Sn_wAl_xSi_y)O_2$; where A is at least one exchangeable cation selected from the group consisting of alkali and alkaline earth metals, "m" is the mole fraction of A and varies from about 0.01 to about 0.49, "w" is the mole fraction of tin and varies from about 0.01 to about 0.49, "x" is the mole fraction of aluminum and varies from about 0.01 to about 0.49, and "y" is the mole fraction of silicon and varies from about 0.50 to about 0.98;

(b) a platinum-group metal component; and, (c) an inorganic-oxide binder.

2. The process of claim 1 wherein the aromatization conditions comprise an operating pressure of from about 100 kPa to about 1.0 MPa, a liquid hourly space velocity of from about 0.5 to 40 $hr^{-1}$ and a temperature of from about 260° to 600° C.

3. The process of claim 2 wherein the operating pressure is from about 100 to 500 kPa.

4. The process of claim 3 wherein the operating pressure is from about 100 to 300 kPa.

5. The process of claim 2 wherein free hydrogen is present in an amount of from about 0.1 to 10 moles per mole of hydrocarbon feedstock.

6. The process of claim 1 wherein the corresponding aromatic isomers comprise at least 80 mass-% of the aromatized product.

7. The process of claim 1 wherein the corresponding aromatic isomers comprise at least 90 mass-% of the aromatized product.

8. The process of claim 1 wherein the paraffinic isomers comprise at least one heptane isomer and the corresponding aromatic isomers comprises toluene.

9. The process of claim 1 wherein the paraffinic isomers comprise at least one octane isomer and the corresponding aromatic isomers comprise one or more of the xylenes and ethylbenzene.

10. The process of claim 1 wherein the paraffinic isomer comprises 2,5-dimethylhexane and the corresponding aromatic isomer comprises paraxylene.

11. The process of claim 1 wherein the platinum-group metal component comprises platinum.

12. The process of claim 1 wherein the mass ratio of tin to platinum-group metal in the catalyst is at least 2.

13. The process of claim 1 wherein the paraffinic isomers consist essentially of heptanes and the aromatic isomer consists essentially of toluene.

14. The process of claim 1 wherein the paraffinic isomers consist essentially of octanes and the aromatic isomers consist essentially of $C_8$ aromatics.

15. The process of claim 1 wherein the paraffinic isomer consists essentially of 2,5-dimethylhexane and the aromatic isomer consists essentially of para-xylene.

16. The process of claim 1 further comprising processing the aromatics-rich effluent in a separation zone to obtain an aromatics concentrate and an aliphatics concentrate, and recycling the aliphatics concentrate to the aromatization zone to obtain additional aromatized product.

17. A process for the aromatization of one or both of heptanes and octanes in a hydrocarbon feedstock comprising contacting the feedstock with an aromatization catalyst in an aromatization zone at aromatization conditions to obtain an aromatics-rich effluent containing an aromatized product comprising at least 70 mass-% of one or both of toluene and $C_8$ aromatics, the catalyst comprising:

(a) a nonacidic L-zeolite having a unit empirical formula on an anhydrous basis of $mA:(Sn_wAl_xSi_y)O_2$; where A is at least one exchangeable cation selected from the group consisting of alkali and alkaline earth metals, "m" is the mole fraction of A and varies from about 0.01 to about 0.49, "w" is the mole fraction of tin and varies from about 0.01 to about 0.49, "x" is the mole fraction of aluminum and varies from about 0.01 to about 0.49, and "y" is the mole fraction of silicon and varies from about 0.50 to about 0.98;

(b) a platinum-group metal component; and, (c) an inorganic-oxide binder.

18. A process for the aromatization of a hydrocarbon feedstock comprising contacting the feedstock with an aromatization catalyst in an aromatization zone at aromatization conditions to obtain an aromatics-rich effluent stream, the catalyst characterized by a method of preparation comprising:

(a) contacting an L-zeolite molecular sieve with a fluoro salt of tin, said fluoro salt being in the form of an aqueous solution or slurry at a pH of about 3 to about 7 to provide a molecular sieve having a unit empirical formula on an anhydrous basis of $mA:(Sn_wAl_xSi_y)O_2$; where A is at least one exchangeable cation selected from the group consisting of alkali and alkaline earth metals, "m" is the mole fraction of A and varies from about 0.01 to about 0.49, "w" is the mole fraction of tin and varies from about 0.01 to about 0.49, "x" is the mole fraction of aluminum and varies from about 0.01 to about 0.49, and "y" is the mole fraction of silicon and varies from about 0.50 to about 0.98;

(b) compositing the molecular sieve with an inorganic binder to form a bound catalyst; and, (c) incorporating a platinum-group metal component and finishing the composite to form a catalyst by one or both of calcination and reduction.

* * * * *